United States Patent [19]

Gereg

[11] 4,430,614
[45] Feb. 7, 1984

[54] EDDY CURRENT BEARING BALL FLAW DETECTOR

[75] Inventor: Charles V. Gereg, Bethel, Conn.

[73] Assignee: The Barden Corporation, Danbury, Conn.

[21] Appl. No.: 214,777

[22] Filed: Dec. 10, 1980

[51] Int. Cl.³ .................... G01N 27/82; G01R 33/00
[52] U.S. Cl. ................................. 324/238; 324/262
[58] Field of Search ............... 324/225, 237, 238, 240, 324/226, 234, 236, 239, 241, 242, 243, 262

[56] References Cited

U.S. PATENT DOCUMENTS

| 2,994,032 | 7/1961 | Hansen | 324/213 |
| 3,921,065 | 11/1975 | Rawling et al. | 324/238 |
| 4,155,455 | 5/1979 | Spierer et al. | 209/558 |
| 4,330,748 | 5/1982 | Holden | 324/225 |

FOREIGN PATENT DOCUMENTS 2103637  8/1972 Fed. Rep. of Germany .
1079913  8/1967 United Kingdom .
1349344  4/1974 United Kingdom .
1381392  1/1975 United Kingdom .

*Primary Examiner*—Gerard R. Strecker
*Assistant Examiner*—Walter E. Snow
*Attorney, Agent, or Firm*—Shenier & O'Connor

[57] ABSTRACT

Apparatus for detecting surface flaws in generally spherical articles such as bearing balls. A spindle carrying a vacuum chuck at one end for gripping the ball is driven to rotate the ball about a first axis. An eddy current probe mounted for rotation about a second axis generally orthogonal to the first axis is urged against the ball to scan a circular strip for cracks and is rotated about the second axis to vary the location of the strip being scanned along the first axis. The probe output is applied through a bandpass filter to a threshold alarm and to the vertical input of an oscilloscope triggered synchronously with the rotation of the spindle.

9 Claims, 4 Drawing Figures

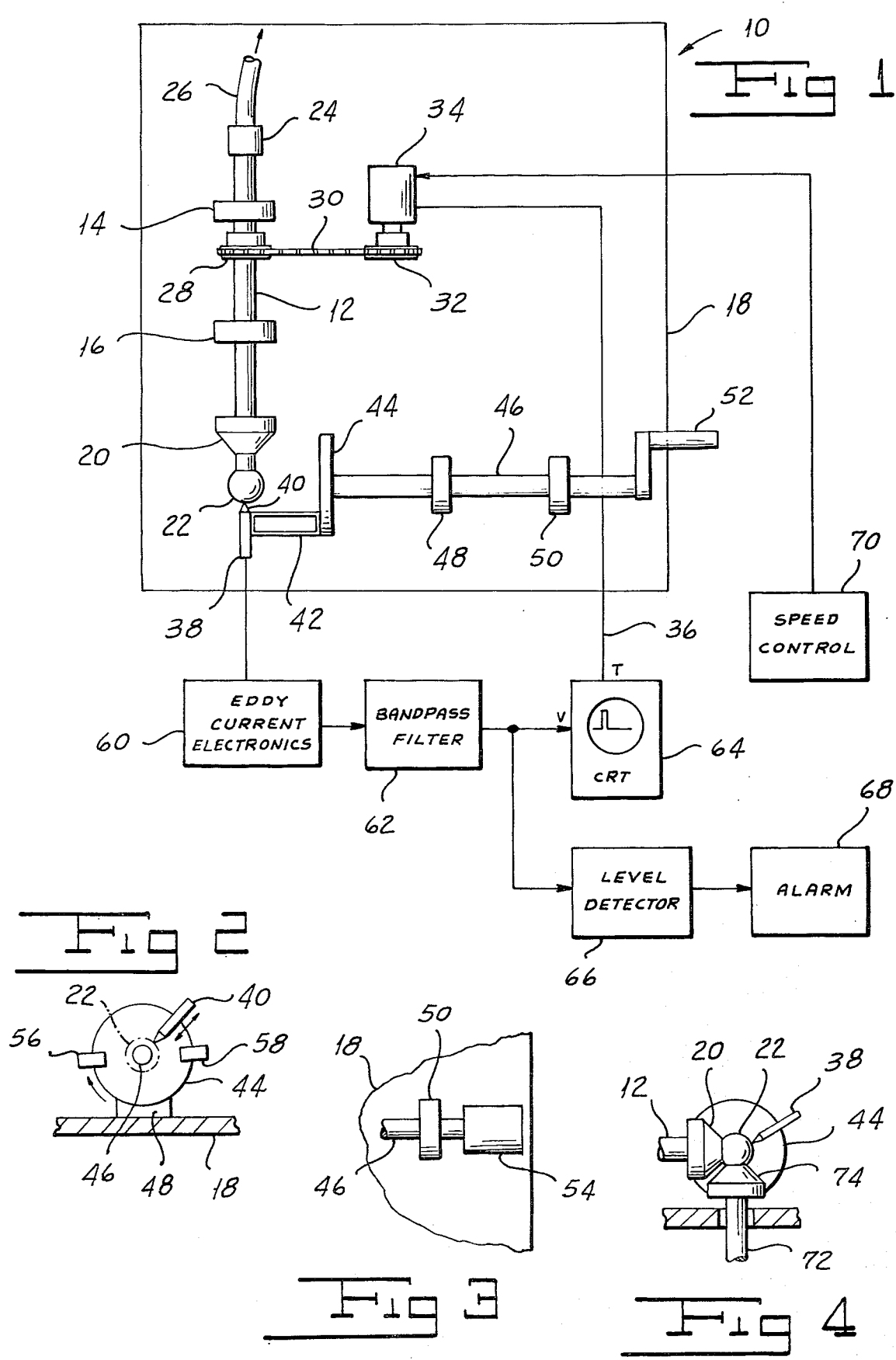

EDDY CURRENT BEARING BALL FLAW
DETECTOR

Field of the Invention

This invention relates to apparatus for detecting flaws in manufactured articles and, especially, to apparatus for detecting flaws by sensing eddy currents in generally spherical articles such as bearing balls.

BACKGROUND OF THE INVENTION

Systems which detect flaws in conductive materials by generating and detecting eddy currents in the materials being tested are well known in the art, being shown, for example, in Hochschild U.S. Pat. No. 2,877,406, Diamond et al U.S. Pat. No. 3,089,084 and Vild et al U.S. Pat. No. 4,123,708. While many of these devices readily test cylindrical articles such as methal rods or tubes, they are not readily adaptable for use with generally spherical articles such as bearing balls.

SUMMARY OF THE INVENTION

One object of my invention is to provide a flaw detector that is especially adaptable for use with generally spherical articles.

Another object of my invention is to provide a flaw detector which operates relatively uniformly over the surface of a sphere.

Still another object of my invention is to provide a flaw detector which is relatively insensitive to variations in material properties of the article being tested which are not the result of flaws.

A further object of my invention is to provide a flaw detector which is simple and inexpensive for the result accomplished thereby.

Other and further objects will be apparent from the following description.

In one aspect, my invention contemplates apparatus for inspecting a generally spherical article for flaws in which the article is rotated about a first axis to cause a suitable probe, such as an eddy current probe, positioned adjacent the surface of the particle to scan a circular strip and in which the probe-positioning assembly is itself rotated about a second axis intersecting, and preferably orthogonal to, the first axis to vary the location of the scanned strip.

In another aspect, my invention contemplates apparatus for inspecting an article for flaws in which the article is rotated about an axis to cause a suitable probe, such as an eddy current probe, positioned adjacent the surface of the article to scan a circular strip and in which the outputs of the probe obtained during successive rotations of the article are correlated. Preferably the probe outputs are correlated by coupling the probe to either the horizontal input or the vertical input of a display and sweeping the other display input synchronously with the rotation of the article.

In yet another aspect, my invention contemplates apparatus for inspecting an article for flaws in which the article is rotated about an axis at a certain frequency to cause a suitable probe, such as an eddy current probe, positioned adjacent the surface of the article to scan a circular strip and in which the probe is coupled to a filter having a lower cutoff frequency substantially greater than the frequency of rotation of the article.

BRIEF DESCRIPTION OF THE DRAWINGS

In the accompanying drawings to which reference is made in the instant specification and in which like reference characters are used to indicate like parts in the various views:

FIG. 1 is a partly schematic top plan of a preferred embodiment of my flaw detector.

FIG. 2 is a fragmentary section of the apparatus shown in FIG. 1, illustrating the probe-positioning subassembly.

FIG. 3 is a fragmentary top plan of a modified form of the apparatus shown in FIG. 1 in which a motor is used to drive the probe-positioning subassembly.

FIG. 4 is a fragmentary section of another modified form of the apparatus shown in FIG. 1 incorporating two ball-rotating assemblies disposed on orthogonal axes.

DESCRIPTION OF THE PREFERRED EMBODIMENTS

Referring now to FIG. 1, my apparatus, indicated generally by the reference character 10, includes a horizontally extending tubular spindle 12 rotatably supported by bearings 14 and 16 upon a base 18. Spindle 12 receives a removable vacuum chuck 20 of suitable size at one end for gripping a ball 22, the surface of which is to be examined for flaws. Preferably, chuck 20 comprises a relatively soft material so as not to scratch the surface of the ball 22 being tested. A rotating coupling 24 at the other end of spindle 12 from chuck 20 connects the interior of the spindle to a vacuum hose 26 coupled to a suitable partial vacuum source (not shown).

Spindle 12 supports a sprocket wheel 28 coupled through a drive chain 30 to another sprocket wheel 32 mounted on the shaft of a variable-speed motor 34. Motor 34 is energized by means of a manually adjustable speed-control unit 70 of any suitable type known to the art. Motor 34 also provides an alternating-current tachometer output on a line 36 that is proportional in amplitude to the speed of the motor 34 and bears a fixed phase relationship to the position of the motor shaft. Preferably sprocket wheels 28 and 32 provide a one-to-one speed ratio so that the signal on line 36 also indicates the angular position of spindle 12.

I position a second spindle 46, rotatably supported by bearings 48 and 50 upon base 18, in such a manner that its axis perpendicularly intersects the axis of spindle 12 at the center of ball 22. A disc 44 mounted on spindle 46 at the end adjacent to the ball 22 supports one end of a parallelarm flexure mount 42, the other end of which is attached to the side of an eddy current probe 38.

Eddy current probe 38 may be of any suitable type known in the art. Specifically, probe 38 may contain either a combined induction and detection coil (not shown), through which an alternating current is passed to induce eddy currents in the region being tested, or, alternatively, separate induction and detection coils (not shown).

Disc 44 supports probe 38 for rotational movement in a vertical plane passing through the center of the ball 22 and through the axis of spindle 12, while flexure mount 42 urges the tip 40 of probe 38 against the ball 22 along a line of action passing through the ball center. By maintaining tip 40 in contact with the ball 22, I avoid variations in output due to variations in spacing between the tip 40 and the ball 22. Preferably, the tip 40 of the probe 38 comprises a low-abrasion material so as not to injure the surface of the ball 22 being tested. Spindle 46 may be rotated either manually by means of a handle 52 mounted on the end remote from ball 22 or automatically by means of a relatively low-speed, torque-limited motor 54 as shown in the modified construction of FIG. 3. A pair of limit stops 56 and 58 which are adjustable circumferentially about the periphery of disc 46 define angular limit positions for rotation of the spindle 46.

It will be apparent from the foregoing description that rotation of the spindle 12 causes the tip 40 of probe 38 to scan a circular strip of the ball 22, while the rotation of the spindle 46 varies the location of the strip latitudinally, that is, along the axis of spindle 12. I couple probe 38 to an eddy current electronics system 60 of any suitable type known in the art, such as an Automation Industries EM 3300 or equivalent.

Eddy currents induced in the ball 22 by the induction coil (not shown) of the probe 38 give rise to an increase in that quadrature component of the detection coil voltage which is in phase with the induction coil current. While the desired quadrature component of the detection coil voltage is, in practice, not precisely in phase with the induction coil current, it may be readily obtained by resolving the detection coil voltage into a "lift-off" component dependent on the proximity of the probe 38 to the ball 22 and a "crack" or "eddy current" component independent of probe position. Such resolution is accomplished by the EM 3300 used for the eddy current electronics system 60. Probe 38 is driven at a frequency selected to obtain the desired depth of penetration of the ball 22 by the alternating magnetic field.

I couple the "crack" component output of eddy current electronics system 60 to the input of a bandpass filter 62 having a passband extending approximately between 400 Hz and 1000 Hz. Filter 62 rejects lower frequency components of the output of circuit 60 that are due to such extraneous factors as heading flow lines, original bar or wire flow lines, or the like, thereby improving the sensitivity of the apparatus 10 to cracks. Preferably, the frequency of rotation of the spindle 12 is no greater than about one-tenth the lowest-frequency portion of the passband of filter 62, or about 40 Hz.

I feed the output of filter 62 to the vertical input of a cathode ray oscilloscope 64, with or without screen storage, which receives a trigger input via line 36 from the motor-tachometer 34. By triggering the oscilloscope 64 synchronously with the rotation of spindle 12, I provide for the repeated display of the crack signal on successive sweeps of the oscilloscope 64, thereby further improving the ability of the system to distinguish cracks from noise. If desired, oscilloscope 64 can also be triggered at a submultiple of the ball-rotation frequency. The output of filter 62 may also feed a level detector 66 which actuates an alarm 68, such as a bell, flashing light or the like, whenever the input to the level detector exceeds a certain threshold. The threshold may be suitably calibrated using either a ball having known cracks or a master with a manufactured defect.

In operation, after the ball 22 is positioned on a chuck of suitable size and motor 34 actuated to drive the ball at a suitable rotational velocity, the probe 38 is moved about the ball 22 by rotating spindle 46 to scan a segment of the ball preferably somewhat greater than 90°. Preferably, speed control 70 unit is adjusted to rotate ball 22 at a predetermined surface velocity to standardize the width and hence harmonic content of the pulses applied to filter 62, allowing the use of a fixed filter. After the segment is scanned, the ball 22 is removed from the chuck 20, rotated by hand about a vertical axis through approximately 90° and refitted on the vacuum chuck 20 for an additional scan. In this manner, the entire surface of the ball 22 is scanned. By scanning a segment of somewhat greater than 90° during each placement of the ball 22, one ensures that the entire ball surface is "seen" by the probe 38 so as to provide some overlap for safety.

If desired, rather than manually rotating the ball 90° about a vertical axis, one may employ an additional spindle 72 and chuck 74 arranged on a vertical axis passing through the ball center, as shown in FIG. 4. In the operation of the modified form of apparatus shown in this figure, the ball 22 is first scanned over a segment of somewhat greater than 90° while being gripped by the vacuum chuck 20. After this initial scan, the vacuum controlling chuck 20 is disabled and the vacuum supply (not shown) controlling chuck 74 is enabled so that the ball 22 is then rotated on a vertical axis.

Using the arrangement described above, I can easily detect open or closed cracks longer than a few thousandths of an inch and more than a few microinches deep without detectable damage to finished balls of the best quality. Further, the object being tested need not be a complete sphere. One may, for example, use the apparatus 10 to test a ball that has had a flat formed on it for hardness, retained austenite or metallurgical structure.

It will be seen that I have accomplished the objects of my invention. My flaw detector is especially adaptable for use with generally spherical articles, and operates relatively uniformly over the surface of a sphere. My flaw detector is relatively insensitive to variations in material properties of the article being tested that are not associated with flaws. Finally, my flaw detector is simple and inexpensive for the result accomplished thereby.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. It is, therefore, to be understood that my invention is not to be limited to the specific details shown and described.

Having thus described my invention what I claim is:

1. Apparatus for inspecting the surface of a generally spherical article having a center including in combination first means operable to rigidly hold said article, an inspection probe, means for positioning said probe in contact with the surface of said article, means for rotating said first means about a first axis passing substantially through said center to cause said probe to scan a strip of said surface, and means including means for revolving said positioning means about a second axis passing substantially through said center to vary the location of said strip.

2. Apparatus as in claim 1 wherein the first means comprises a chuck.

3. Apparatus as in claim 1 wherein the first means comprises a vacuum chuck.

4. Apparatus as in claim 1 wherein the positioning means includes means resiliently biasing the probe against said surface with a constant force.

5. Apparatus as in claim 1 wherein the first and second axes are substantially orthogonal.

6. Apparatus as in claim 1 further including display means having horizontal and vertical inputs, means coupling the probe to one input, and means for initiating a sweep of the other input upon successive rotations of said first means through a predetermined integral number of revolutions.

7. Apparatus as in claim 1 further including second means selectively operable to rigidly hold the article, and means for rotating the second means about a third axis passing substantially through said center.

8. Apparatus as in claim 7 wherein the first and second and third axes are substantially orthogonal.

9. Apparatus as in claim 7 wherein the first and second means each comprise a vacuum chuck.

* * * * *